(12) United States Patent
Shivakumar et al.

(10) Patent No.: US 9,765,108 B2
(45) Date of Patent: Sep. 19, 2017

(54) FORMULATION OF 5-AZACYTIDINE

(71) Applicant: SHILPA MEDICARE LIMITED, Karnataka (IN)

(72) Inventors: Pradeep Shivakumar, Vizianagaram (IN); Nagaraju Dasari, Vizianagaram (IN); Ravi Kishore, Vizianagaram (IN); Rizwan Ahmed, Vizianagaram (IN); Akshaykant Chaturvedi, Raichur (IN)

(73) Assignee: SHILPA MEDICARE LIMITED, Karnataka ( * ) Notice: Subject to any disclaimer, the term of this patent is extended or adjusted under 35 U.S.C. 154(b) by 96 days.

(21) Appl. No.: 14/441,517

(22) PCT Filed: Nov. 8, 2013

(86) PCT No.: PCT/IB2013/059992
§ 371 (c)(1),
(2) Date: May 8, 2015

(87) PCT Pub. No.: WO2014/076616
PCT Pub. Date: May 22, 2014

(65) Prior Publication Data
US 2015/0284421 A1    Oct. 8, 2015

(30) Foreign Application Priority Data

Nov. 19, 2012 (IN) .......................... 4801/CHE/2012
May 15, 2013 (IN) .......................... 2148/CHE/2013

(51) Int. Cl.
*C07H 19/12* (2006.01)
*A61K 45/06* (2006.01)

(52) U.S. Cl.
CPC ............. *C07H 19/12* (2013.01); *A61K 45/06* (2013.01)

(58) Field of Classification Search
CPC .................................. A61K 45/06; C07H 19/12
See application file for complete search history.

(56) References Cited

U.S. PATENT DOCUMENTS

| 4,684,630 | A | 8/1987 | Repta et al. |
|---|---|---|---|
| 6,887,855 | B2 | 5/2005 | Ionescu et al. |
| 6,943,249 | B2 | 9/2005 | Ionescu et al. |
| 7,759,481 | B2 * | 7/2010 | Gavenda ................ C07H 19/12 536/25.4 |
| 7,772,199 | B2 | 8/2010 | Ionescu et al. |
| 9,393,255 | B2 * | 7/2016 | Tutino ................. A61K 9/0019 |
| 2011/0042247 | A1 | 2/2011 | Kocherlakota et al. |
| 2012/0196823 | A1 | 8/2012 | Tutino et al. |

FOREIGN PATENT DOCUMENTS

| WO | 2013012135 A1 | 1/2013 |
|---|---|---|
| WO | 2013117969 A1 | 8/2013 |

OTHER PUBLICATIONS ( R ) Gennaro et al., Remington's Pharmaceutical Science, 20th Edition., Philadelphia, PA, 2000, only pp. 802-803, 808-809 and 1484 supplied.*
Kenneth K. Chan et al, 5-Azacytidine Hydrolysis Kinetics Measured by High-pressure Liquid Chromatography and 13C-NMR Spectroscopy, Journal of Pharmaceutical Sciences, Jul. 1979, pp. 807-812, vol. 68 No. 7.
John A. Beisler et al, Isolation Characterization and Properties of a Labile Hydrolysis Product of the Antitumor Nucleoside 5-Azacytidine,Journal of Medicinal Chemistry, 1978, pp. 204-208, vol. 21 No. 2.

* cited by examiner

*Primary Examiner* — Lawrence E Crane

(57) ABSTRACT

The present invention relates to polymorphic forms of 5-Azacytidine and the process for preparation thereof. The present invention further relates to Crystalline 5-azacytidine 5 designated as Form-SA-1 characterized by an X-ray powder diffraction pattern having at least four characteristic diffraction angle peaks at about 12.00, 12.60, 13.90, 15.15 and 31.40±0.20 2θ°, which is useful as active pharmaceutical ingredient in pharmaceutical compositions for the treatment of myelodysplastic syndrome.

5 Claims, 7 Drawing Sheets

FORMULATION OF 5-AZACYTIDINE

CROSS-REFERENCE TO RELATED APPLICATIONS

This present application is a U.S. National Stage Entry of international application PCT/IB2013/059992 filed on Nov. 8, 2013 that claims the priority to Indian Patent Applications 4801/CHE/2012 filed on Nov. 19, 2012 & 2148/CHE/2013 filed on May 15, 2013.

FIELD OF THE INVENTION

The present invention relates to lyophilized formulations comprising Crystalline 5-azacytidine and process for preparing lyophilized formulations comprising Crystalline 5-azacytidine.

BACK GROUND OF THE INVENTION 5-azacytidine (also known as azacitidine 4-amino-1-β-D-ribofuranosyl-1,3,5-triazin-2(1H)-one; Nation Service Center designation NSC-102816; CAS Registry Number 320-67-2) has undergone NCI-sponsored clinical trials for the treatment of myelodysplastic syndromes (MDS). See Komblith et al., J. Clin. Oncol. 20(10): 2441-2452 (2002) and Silverman et al., J. Clin. Oncol. 20(10): 2429-2440 (2002). 5-azacytidine may be defined as having a formula of $C_8H_{12}N_4O_5$, a molecular weight of 244.20 and a structure of:

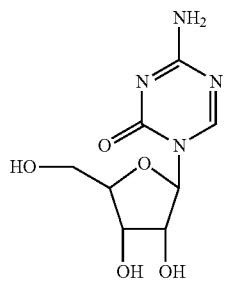 [SMILES: Nc1ncn(C2OC(CO)C(O)C2O)c(=O)n1]

5-azacytidine (5-AZT) is insoluble in acetone, ethanol, and methyl ethyl ketone, slightly soluble in ethanol and water (50:50), propylene glycol, and polyethylene glycol, sparingly soluble in water, water saturated octanol, 5% dextrose in water, N-methylpyrrolidone, normal saline, and 5% Tween™ 80 in water, and soluble in dimethylsulfoxide (DMSO). Azacitidine is used in the treatment of myelodysplastic syndrome.

5-azacytidine is believed to exert its antineoplastic effects by causing hypomethylation of DNA and direct cytotoxicity on abnormal hematopoietic cells in the bone marrow. Hypomethylation may restore normal functions to genes that are critical for differentiation and proliferation. The cytotoxic effects of azacitidine cause the death of rapidly dividing cells, including cancer cells that are no longer responsive to normal growth control mechanism. Non-proliferating cells are relatively insensitive to azacitidine.

A commercially available product containing azacitidine is sold as VIDAZA®, 5-azacytidine for injection, by Celgene. The VIDAZA® product received marketing approval in the U.S. in 2004 and is supplied in a sterile form for reconstitution as a suspension for subcutaneous injection, or reconstitution as a solution with further dilution for intravenous infusion. Vials of the VIDAZA® product contain 100 mg of azacitidine and 100 mg of mannitol, as a sterile lyophilized powder.

5-Azacytidine is approved for subcutaneous (SC) or intravenous (IV) administration to treat various proliferative disorders. The s-triazine ring of 5-azacytidine has a particular sensitivity to water. See, e.g., Beisler, J. Med. Chem., 1978, 21(2), 204-08; Chan, et al., J. Pharm. Sci., 1979, 68(7), 807-12. Azacitidine rapidly degrades in aqueous solution via hydrolysis. (In an aqueous environment both in vivo and in vitro, 5-azacytidine underwent a spontaneous hydrolysis and resulted in an equilibration with a labile product, n-formylguanyl-ribosylurea, and finally the irreversible formation of guanyl-ribosylurea). Due to this instability, an aqueous formulation was not a viable option. Thus, a lyophilized dosage form was developed to minimize water activity in the medicinal product. To minimize azacitidine degradation during product manufacturing, the manufacturing process was developed such that compounding, filtration and filling operations are performed as a continuous process at reduced temperatures.

U.S. Pat. No. 6,887,855 Dumitru et al; reported that 5-azacytidine exists in at least eight different polymorphic and pseudopolymorphic crystalline forms (Forms I-VIII), in addition to an amorphous form. Form I is a polymorph found in prior art retained samples of 5-azacytidine drug substance. Form II is a polymorph found in some prior art retained samples of the 5-azacytidine drug substance; in those samples, Form II is always found in mixed phase with Form I. Form III is a hydrate, and is formed when prior art retained and current samples of the drug product are reconstituted with water to form a "slurry" prior to administration to the patient. Form VI is found in prior art retained samples of the 5-azacytidine drug product, either substantially free of other polymorphs, or in mixed phase with Form I. The invention provides novel crystalline forms referred to as Form IV, Form V, Form VII and Form VIII. Forms I-VIII each have characteristic X-ray power diffraction (XRPD) patterns and are easily distinguished from one another using XRPD. U.S. Pat. No. 7,772,199 Dumitru et al; relates to amorphous solid 5-azacytidine, prepared by a method comprising adding solid 5-azacytidine to a solvent selected from propylene glycol, polyethylene glycol, and DMSO; allowing equilibration to occur; and recovering 5-azacytidine therefrom.

U.S. Pat. No. 6,943,249 Dumitru et al; includes methods for isolating crystalline Form I of 5-azacytidine substantially free of other forms, and also pharmaceutical compositions comprising Form I of 5-azacytidine. The method includes isolating crystalline Form I of 5-azacytidine substantially free of other forms, the method comprising: recrystallizing 5-azacytidine from a solvent mixture comprising at least one primary solvent and at least one co-solvent selected from the group consisting of $C_2$-$C_5$ alcohols, aliphatic ketones, and alkyl cyanides, by cooling said solvent mixture from a temperature selected to allow said 5-azacytidine to dissolve completely to about ambient temperature; and isolating the recrystallized 5-azacytidine. The polar aprotic solvent described as dimethylsulfoxide, dimethylformamide, dimethylacetamide, and N-methylpyrrolidinone.

U.S. Pat. No. 4,684,630 Arnold et al; discloses a method of intravenously injecting an aqueous unstable anticancer agent into a warm-blooded mammal, the agent being selected from the group consisting of 5-azacytosine arabinoside and 5-azacytidine, comprising in combination the following steps:
(a) aqueously diluting a stable, anhydrous organic solution to form an organic-aqueous solution, the organic solution consisting of the agent and a highly water soluble organic solvent selected from the group consisting of dimethylsulfoxide and dimethylacetamide, the organic-aqueous solution having the organic solvent present in a concentration of less than about 5% based on the total weight of the organic-aqueous solution, the organic-aqueous solution being physiologically suitable for intravenous injection into the warm-blooded mammal, the agent being present in the organic-aqueous solution in an effective dosage concentration per unit volume of approximately 1 mg./ml.; and
(b) intravenously injecting the organic-aqueous solution into the warm-blooded mammal; the dilution step occurring immediately prior to the intravenous injection step.

U.S. Publication No. 2011/0042247 Chandrasekhar et al; relates to a pharmaceutical formulation for parenteral administration comprising azacitidine, prepared by a process comprising preparing an aqueous solution containing azacitidine at about −3° C. to about −1° C.; and lyophilizing the solution.

U.S. Publication No. 2012/0196823 Anthony et al; relates to a liquid pharmaceutical composition comprising a cytidine analog selected from 5-azacytidine and Decitabine, and cold sterile water, which is substantially free of impurities.

WO 2013/012135 Kim, Je Hak et al; provides a pre-freeze dried azacitidine preparation, in which azacitidine is dissolved in an aqueous solution comprising 40 to 60 (v/v) % of tertiary butanol, and a method of manufacturing the freeze dried azacitidine preparation. The pre-freeze dried azacitidine preparation of the present invention has improved stability in an aqueous solution. When the pre-freeze dried azacitidine preparation is frozen and dried under predetermined process conditions including a freeze drying cycle, a stability-improved freeze dried azacitidine preparation can be usefully produced.

WO 2013/117969 Khattar, Dhiraj et al; provides a process of preparing a stable pharmaceutical composition of compounds which are susceptible to hydrolysis comprising a. Addition of required quantity of pharmaceutically acceptable lyophilization excipients optionally in Water for Injection in a formulation vessel; b. Addition of organic solvent to form a appropriate proportion of aqueous and organic solvent; c. Maintaining the temperature of the formulation vessel from the range −5±1° C. to −5±3° C.; d. Addition of required quantity of compound susceptible to hydrolysis to form a solution and lyophilizing the solution.

Therefore, a great need remains for lyophilized formulations of cytidine analogs (e.g., 5-azacytidine) and methods of preparing and using such lyophilized formulations, or new polymorphs in such formulations to potentially permit, inter alia, for convenient administration to patients, and limited amount of impurities upon storage, wherein the suitable impurity profile is also to minimize potential toxicity, and ensure accurate delivery of intended dose of cytidine analogs for treating new diseases or disorders or new patient populations; and/or other potential advantageous benefits.

SUMMARY OF THE INVENTION

Provided herein are lyophilized formulations comprising 5-azacytidine crystalline forms. Also provided are methods of preparing the said formulations, and methods of using the formulations to treat disorders related to abnormal cell proliferation including cancer and hematologic disorders.

Aspects of the present invention relate to a pre-lyophilized pharmaceutical compositions comprising 5-azacytidine, in a stabilizing amount of solvent vehicle comprising at least one organic solvent selected from acetonitrile, tertiary-butyl alcohol, ethanol and acetone; and refrigerated water.

Aspects of the present invention relate to a crystalline 5-Azacytidine designated as Form-SA-1 characterized by an X-Ray powder diffraction pattern having at least four characteristic diffraction angle peaks at about 12.00, 12.60, 13.90, 15.15 and 31.40±0.20 2θ°.

Aspects of the present invention relate to a crystalline 5-Azacytidine Form-SA-1 having water content less than 1%.

Aspects of the present invention relate to a process for preparing crystalline 5-Azacytidine Form SA-1, comprising the steps of—
(i) Dissolving 5-azacytidine in a solvent vehicle comprising acetonitrile and refrigerated water in the ratio of 20:80 to 60:40, to get clear solution.
(ii) Freeze-drying the solution,
(i) Isolating the Crystalline 5-Azacytidine Form SA-1.

Aspects of the present invention relate to a process for preparing Crystalline 5-Azacytidine Form SA-1, comprising the steps of—
(i) Dissolving 5-azacytidine in a solvent vehicle comprising acetonitrile and refrigerated water in the ratio of 20:80 to 60:40, to get clear solution, at a temperature of less than 5° C., and under nitrogen purging.
(ii) Freeze-drying the solution,
(ii) Isolating the Crystalline 5-Azacytidine Form SA-1.

Aspects of the present invention relate to a lyophilized formulation comprising crystalline 5-Azacytidine Form-SA-1, characterized by an X-Ray powder diffraction pattern having at least four characteristic diffraction angle peaks at about 12.00, 12.60, 13.90, 15.15 and 31.40±0.20 2θ°, optionally a bulking agent; and having water content less than 1%.

Aspects of the present invention relate to a process for preparing lyophilized formulation comprising Crystalline 5-Azacytidine Form SA-1, characterized by the steps:
(i) Dissolving optional bulking agent and 5-azacytidine, in a stabilizing amount of solvent vehicle comprising acetonitrile and refrigerated water; in the ratio of 20:80 to 60:40.
(ii) Lyophilizing the solution obtained from step (i);
wherein the said lyophilized formulation having 1-β-D-ribofuranosyl-3-guanylurea (RGU) impurity not more than 0.2% and total impurities not more than 2%.

Aspects of the present invention relate to a crystalline 5-Azacytidine designated as Form-SA-2, characterized by an X-Ray powder diffraction angle peaks at about 6.9, 14.0, 17.9 and 24.2°±0.20 2θ°, and having water content less than 1%.

Aspects of the present invention relate to a process for preparing lyophilized formulation comprising Crystalline 5-Azacytidine Form SA-2, characterized by the steps:
(i) Dissolving optional bulking agent and 5-azacytidine in a solvent vehicle comprising tertiary butanol and refrigerated water in the ratio of 30:70.
(ii) Freeze-drying the solution,
(iii) Isolating the Crystalline 5-Azacytidine Form SA-2.

Aspects of the present invention relate to a lyophilized formulation comprising crystalline 5-Azacytidine Form-SA-2, characterized by an X-Ray powder diffraction pattern having at least four characteristic diffraction angle peaks at about 6.9, 14.0, 17.9 and 24.2°±0.20 2θ°, optionally a bulking agent; and having water content less than 1%.

Aspects of the present invention, relates to a lyophilized formulation comprising 5-Azacytidine Form SA-1 or 5-Azacytidine Form SA-2 for parenteral administration, in a sterile vessel is provided, comprising 5-azacytidine for administration to a subject in need thereof. The sterile vessel comprising a pharmaceutical formulation according to the present invention; for example, may be a vial, syringe, or ampoule.

Aspects of the present invention, herein relates to methods of using the lyophilized formulation comprising 5-Azacytidine Form SA-1 or 5-Azacytidine Form SA-2 for parenteral administration, provided herein to treat diseases or disorders including, e.g., cancer, disorders related to abnormal cell proliferation, hematologic disorders, or immune disorders, among others. In certain embodiments, the pharmaceutical compositions of 5-azacytidine which are parenterally administered to subjects in need thereof to treat a cancer or a hematological disorder, such as, for example, Myelodysplastic syndromes (MDS), acute myelogenous leukemia (AML).

| S. no. | Angle 2-Θ° |
|---|---|
| 1. | 6.35 |
| 2. | 12.025 |
| 3. | 12.246 |
| 4. | 12.707 |
| 5. | 13.104 |
| 6. | 14.484 |
| 7. | 15.173 |
| 8. | 16.551 |
| 9. | 17.475 |
| 10. | 18.547 |
| 11. | 18.724 |
| 12. | 19.131 |
| 13. | 20.274 |
| 14. | 20.81 |
| 15. | 21.407 |
| 16. | 21.652 |
| 17. | 22.812 |
| 18. | 23.132 |
| 19. | 23.306 |
| 20. | 23.971 |
| 21. | 24.626 |
| 22. | 24.989 |
| 23. | 25.515 |
| 24. | 26.224 |
| 25. | 26.49 |
| 26. | 26.952 |
| 27. | 27.231 |
| 28. | 27.711 |
| 29. | 28.75 |
| 30. | 29.158 |
| 31. | 29.386 |
| 32. | 29.683 |
| 33. | 30.185 |
| 34. | 30.457 |
| 35. | 31.918 |
| 36. | 32.173 |
| 37. | 32.912 |
| 38. | 33.14 |
| 39. | 33.722 |
| 40. | 34.873 |
| 41. | 36.896 |
| 42. | 37.563 |
| 43. | 37.942 |
| 44. | 38.825 |
| 45. | 40.217 |
| 46. | 40.761 |
| 47. | 41.744 |
| 48. | 43.304 |
| 49. | 43.472 |
| 50. | 45.582 |
| 51. | 46.086 |
| 52. | 46.609 |
| 53. | 47.908 |

Figure 2:
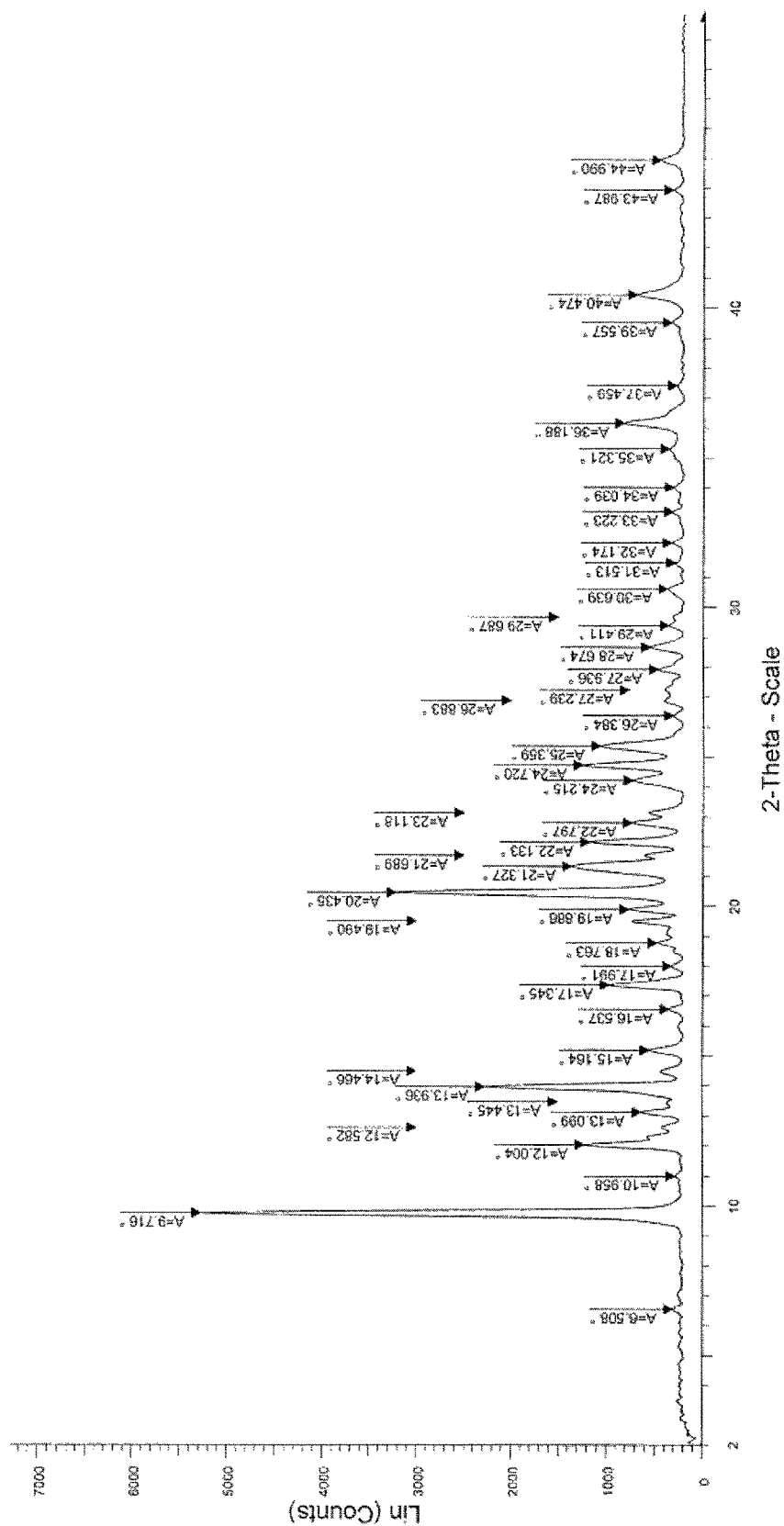

FIG. 2 is Illustration of X-ray powder diffraction (XRPD) pattern of 5-Azacytidine formulation of example 1 containing 5-Azacytydine SA-1.

Figure 3:
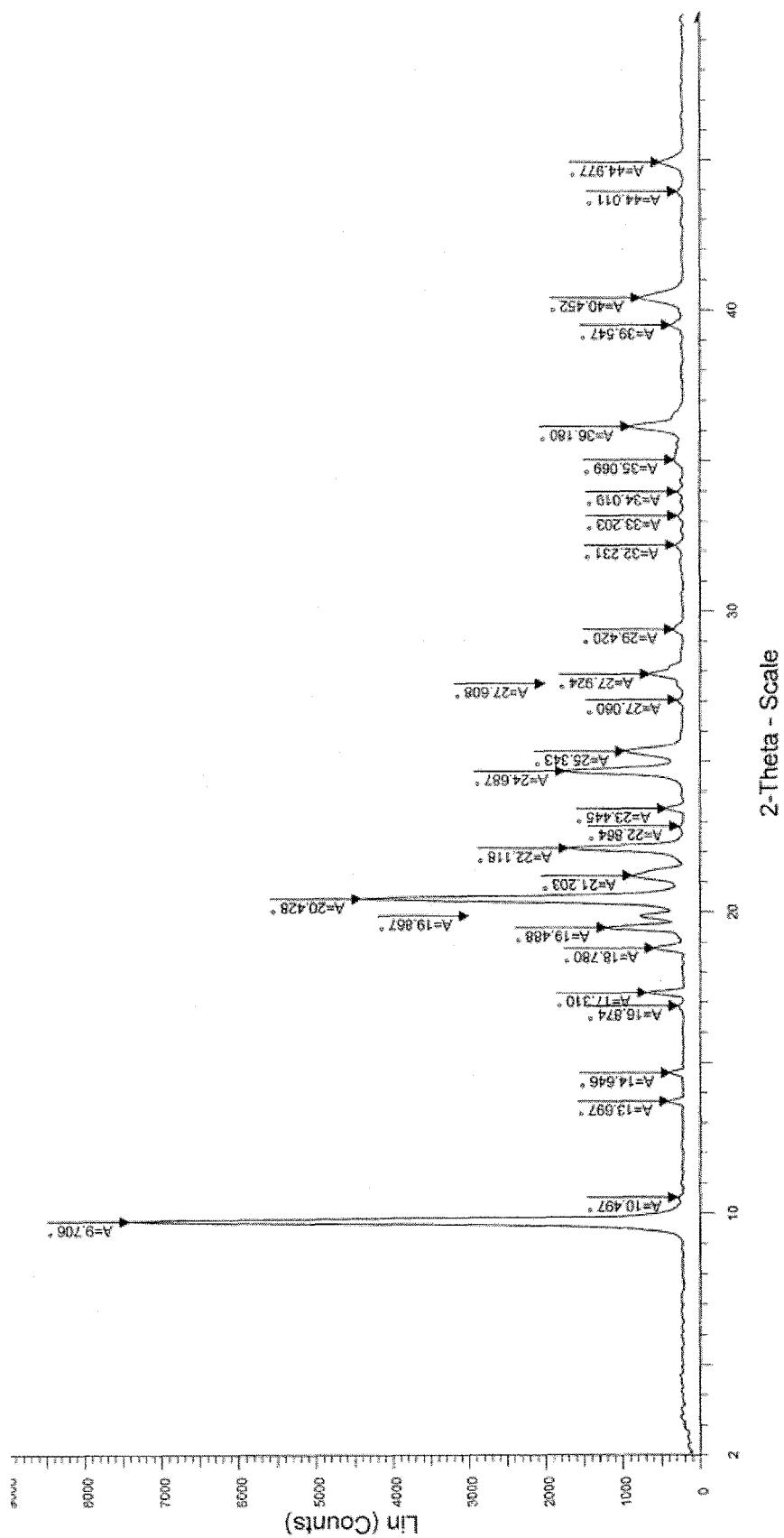

FIG. 3 is Illustration of X-ray powder diffraction (XRPD) pattern of placebo formulation of example 1.

Figure 1:
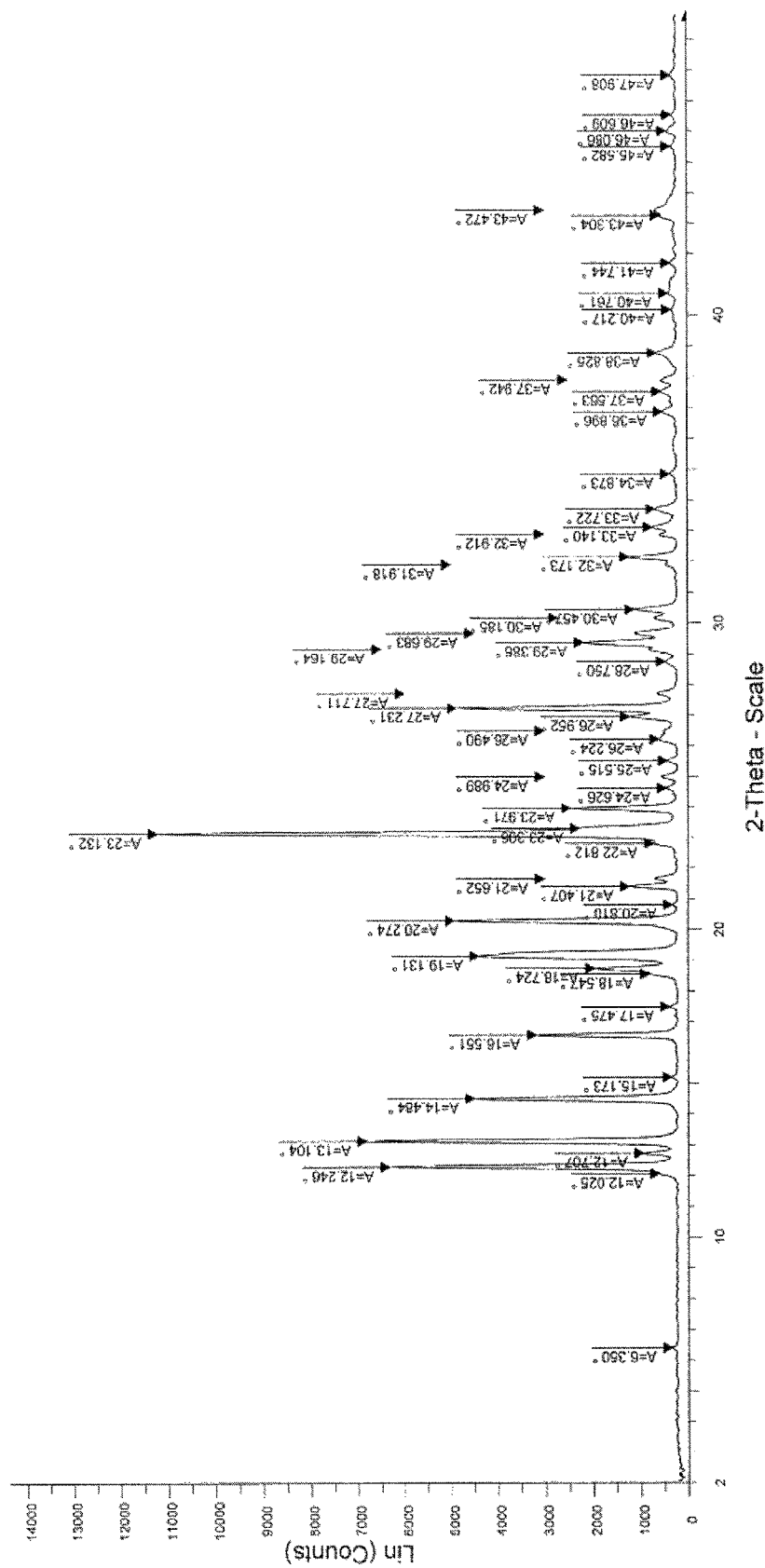
FIG. 1 is Illustration of X-ray powder diffraction (XRPD) pattern of Crystalline 5-Azacytydine Form I.
X-Ray powder diffraction pattern of Form-I provided under the table below.

Comparative X-Ray powder diffraction patterns of lyophilized formulation of example 1 containing crystalline Form-SA-1, as against Form I, and placebo lyophilized formulation of example 1; are provided under the below table:

| XRPD peaks 2-θ° values of (FIG. 1). Angle 2-Θ° | XRPD peaks 2-θ° values of (FIG. 2). Angle 2-Θ° | XRPD peaks 2-θ° values of (FIG. 3). Angle 2-Θ° |
|---|---|---|
| 6.35 | 6.508 | 9.706 |
| 12.025 | 9.716 | 10.497 |
| 12.246 | 10.958 | 13.697 |
| 12.707 | 12.004 | 14.646 |
| 13.104 | 12.582 | 16.874 |
| 14.484 | 13.099 | 17.310 |
| 15.173 | 13.445 | 18.780 |
| 16.551 | 13.936 | 19.488 |
| 17.475 | 14.466 | 19.867 |
| 18.547 | 15.164 | 20.428 |
| 18.724 | 16.537 | 21.203 |
| 19.131 | 17.345 | 22.118 |
| 20.274 | 17.991 | 22.064 |
| 20.81 | 18.763 | 23.445 |
| 21.407 | 19.490 | 24.687 |
| 21.652 | 19.886 | 25.343 |
| 22.812 | 20.435 | 27.060 |
| 23.132 | 21.327 | 27.608 |
| 23.306 | 21.689 | 27.924 |
| 23.971 | 22.133 | 29.420 |
| 24.626 | 22.797 | 32.231 |
| 24.989 | 23.118 | 33.203 |
| 25.515 | 24.215 | 34.019 |
| 26.224 | 24.720 | 35.069 |
| 26.49 | 25.359 | 36.180 |
| 26.952 | 26.384 | 39.547 |
| 27.231 | 26.883 | 40.452 |
| 27.711 | 27.239 | 44.011 |
| 28.75 | 27.936 | 44.977 |
| 29.158 | 28.674 | — |
| 29.386 | 29.411 | — |
| 29.683 | 29.687 | — |
| 30.185 | 30.639 | — |
| 30.457 | 31.513 | — |
| 31.918 | 32.174 | — |
| 32.173 | 33.223 | — |
| 32.912 | 34.039 | — |
| 33.14 | 35.321 | — |
| 33.722 | 36.188 | — |

-continued

| XRPD peaks 2-Θ° values of (FIG. 1). Angle 2-Θ° | XRPD peaks 2-Θ° values of (FIG. 2). Angle 2-Θ° | XRPD peaks 2-Θ° values of (FIG. 3). Angle 2-Θ° |
|---|---|---|
| 34.873 | 37.459 | — |
| 36.896 | 39.557 | — |
| 37.563 | 40.474 | — |
| 37.942 | 43.987 | — |
| 38.825 | 44.990 | — |
| 40.217 | — | — |
| 40.761 | — | — |
| 41.744 | — | — |
| 43.304 | — | — |
| 43.472 | — | — |
| 45.582 | — | — |
| 46.086 | — | — |
| 46.609 | — | — |
| 47.908 | — | — |

Figure 4:
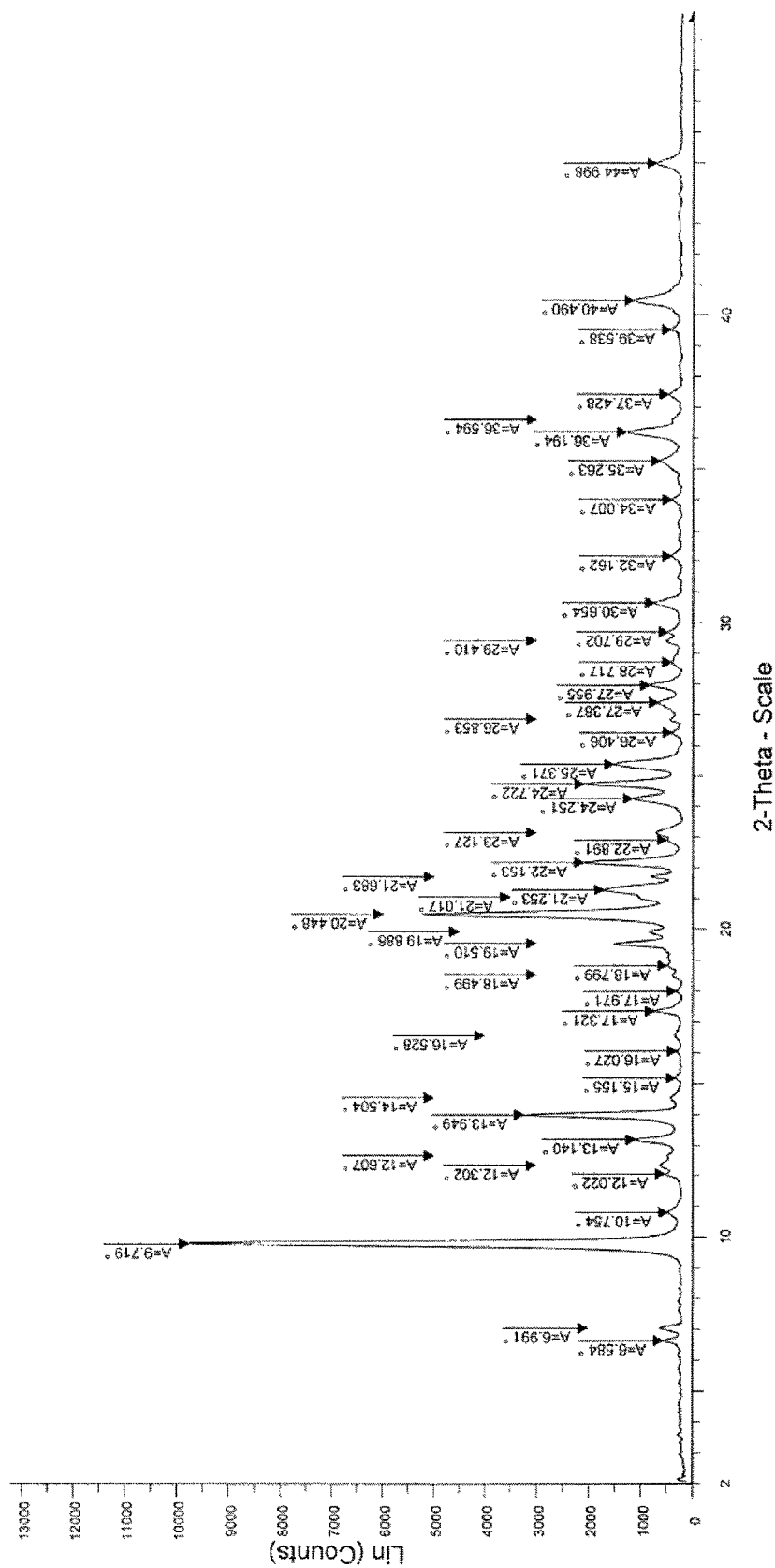

FIG. 4 is Illustration of X-ray powder diffraction (XRPD) pattern of 5-Azacytydine formulation of example 2 containing 5-Azacytydine SA-2.

Figure 5:
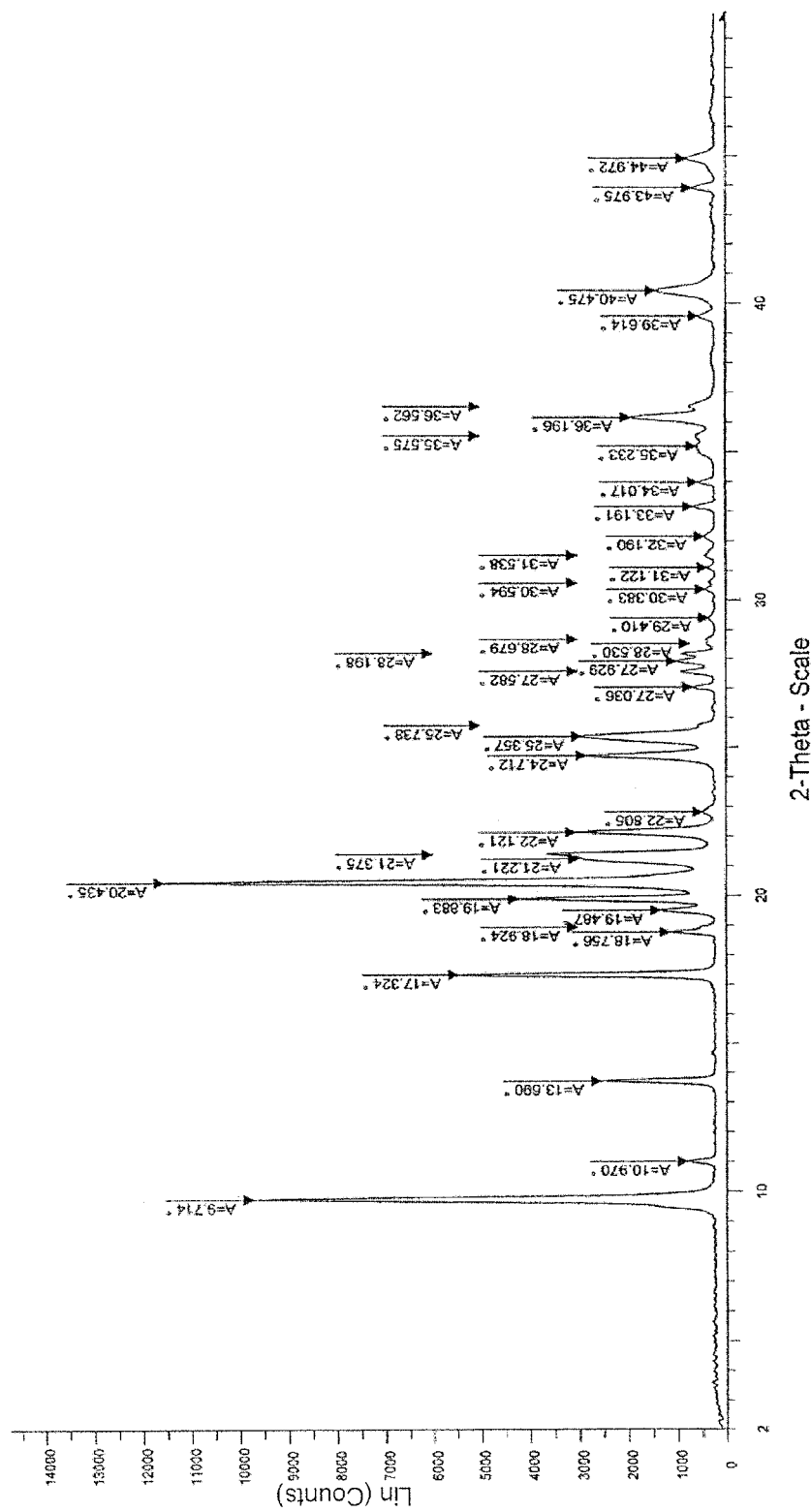

FIG. 5 is Illustration of X-ray powder diffraction (XRPD) pattern of placebo formulation of example 2.

Comparative X-Ray powder diffraction patterns of lyophilized formulation of example 2 containing crystalline Form-SA-2, as against Form I, and placebo lyophilized formulation of example 2; are provided under the below table:

| XRPD peaks 2-Θ° values of (FIG. 1). | XRPD peaks 2-Θ° values of (FIG. 4). Angle 2-Θ° | XRPD peaks 2-Θ° values of (FIG. 5). Angle 2-Θ° |
|---|---|---|
| 6.35 | | |
| 12.025 | 6.584 | 9.714 |
| 12.246 | 6.991 | 10.97 |
| 12.707 | 9.719 | 13.69 |
| 13.104 | 10.754 | 17.324 |
| 14.484 | 12.022 | 18.756 |
| 15.173 | 12.302 | 18.924 |
| 16.551 | 12.607 | 19.487 |
| 17.475 | 13.14 | 19.883 |
| 18.547 | 13.949 | 20.435 |
| 18.724 | 14.504 | 21.221 |
| 19.131 | 15.155 | 21.375 |
| 20.274 | 16.027 | 22.121 |
| 20.81 | 16.528 | 22.805 |
| 21.407 | 17.321 | 24.712 |
| 21.652 | 17.971 | 25.357 |
| 22.812 | 18.499 | 25.738 |
| 23.132 | 18.799 | 27.036 |
| 23.306 | 19.51 | 27.582 |
| 23.971 | 19.886 | 27.929 |
| 24.626 | 20.448 | 28.198 |
| 24.989 | 21.017 | 28.53 |
| 25.515 | 21.253 | 28.679 |
| 26.224 | 21.683 | 29.41 |
| 26.49 | 22.153 | 30.383 |
| 26.952 | 22.891 | 30.594 |
| 27.231 | 23.127 | 31.122 |
| 27.711 | 24.251 | 31.538 |
| 28.75 | 24.722 | 32.19 |
| 29.158 | 25.371 | 33.191 |
| 29.386 | 26.406 | 34.017 |
| 29.683 | 26.853 | 35.233 |
| 30.185 | 27.387 | 35.575 |
| 30.457 | 27.955 | 36.196 |
| 31.918 | 28.717 | 36.562 |
| 32.173 | 29.41 | 39.614 |
| 32.912 | 29.702 | 40.475 |
| 33.14 | 30.654 | 43.975 |
| 33.722 | 32.162 | 44.972 |
| 34.873 | 34.007 | — |
| 36.896 | | |

| XRPD peaks 2-Θ° values of (FIG. 1). | XRPD peaks 2-Θ° values of (FIG. 4). | XRPD peaks 2-Θ° values of (FIG. 5). |
|---|---|---|
| 37.563 | 35.263 | — |
| 37.942 | 36.194 | — |
| 38.825 | 36.594 | — |
| 40.217 | 37.428 | — |
| 40.761 | 39.538 | — |
| 41.744 | 40.49 | — |
| 43.304 | 44.998 | — |
| 43.472 | — | — |

Figure 6:
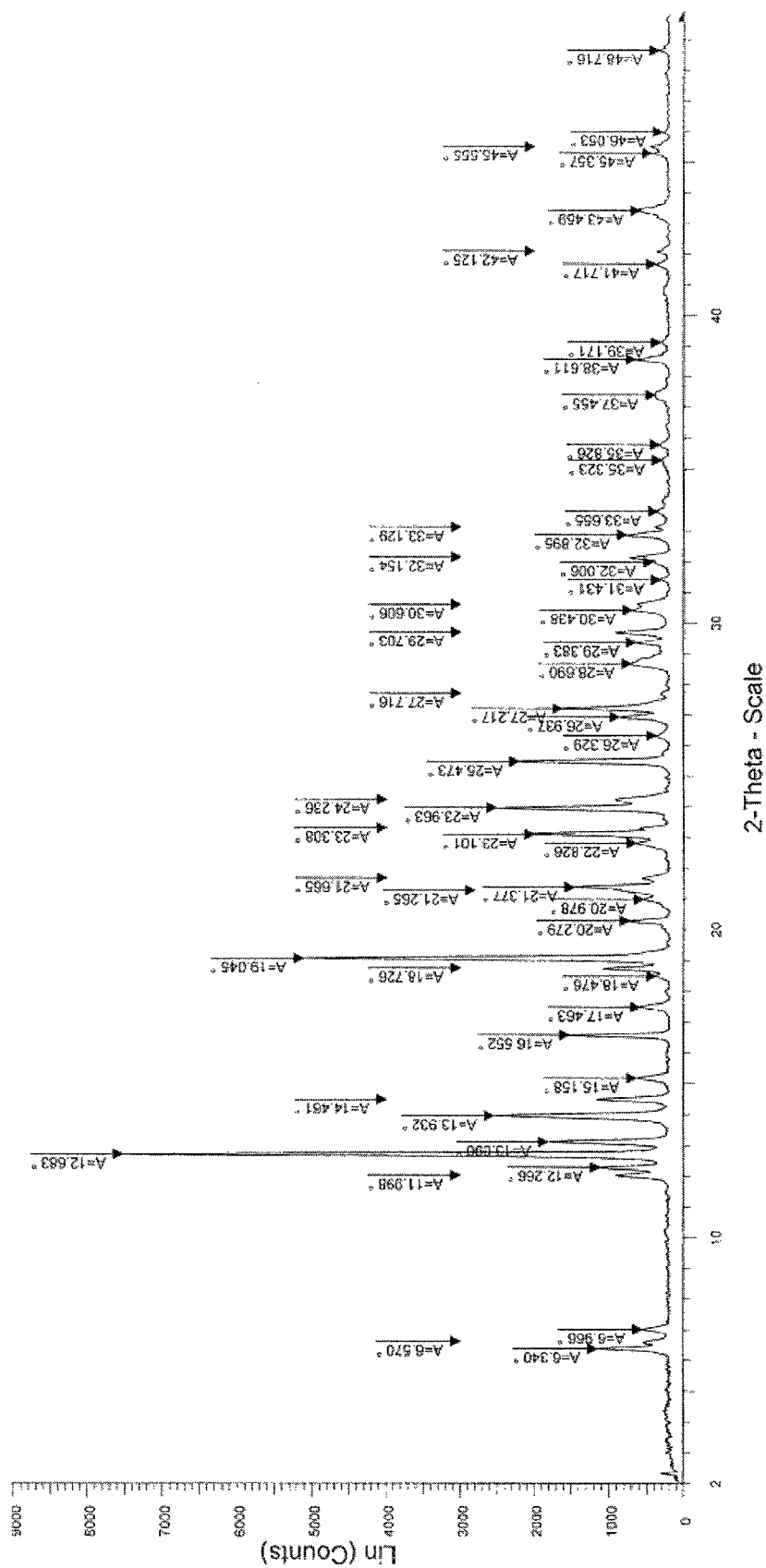

FIG. 6 is Illustration of X-ray powder diffraction (XRPD) pattern of formulation containing Neat Crystalline 5-Azacytidine Form SA-1 prepared in example 3.

X-Ray powder diffraction pattern of Neat Crystalline 5-Azacytidine Form SA-1 provided under the table below:

| Angle 2-Θ° |
|---|
| 6.340 |
| 6.570 |
| 6.966 |
| 11.998 |
| 12.266 |
| 12.683 |
| 13.090 |
| 13.932 |
| 14.461 |
| 15.158 |
| 16.552 |
| 17.463 |
| 18.476 |
| 18.726 |
| 19.045 |
| 20.279 |
| 20.978 |
| 21.265 |
| 21.377 |
| 21.665 |
| 22.826 |
| 23.101 |
| 23.308 |
| 23.963 |
| 24.236 |
| 25.473 |
| 26.329 |
| 26.937 |
| 27.217 |
| 27.716 |
| 28.690 |
| 29.383 |
| 29.703 |
| 30.438 |
| 30.606 |
| 31.431 |
| 32.006 |
| 32.154 |
| 32.895 |
| 33.129 |
| 33.655 |
| 35.323 |
| 35.826 |
| 37.455 |
| 38.611 |
| 39.171 |
| 41.717 |
| 42.125 |
| 43.459 |
| 45.357 |
| 45.555 |
| 46.053 |
| 48.716 |

Figure 7:
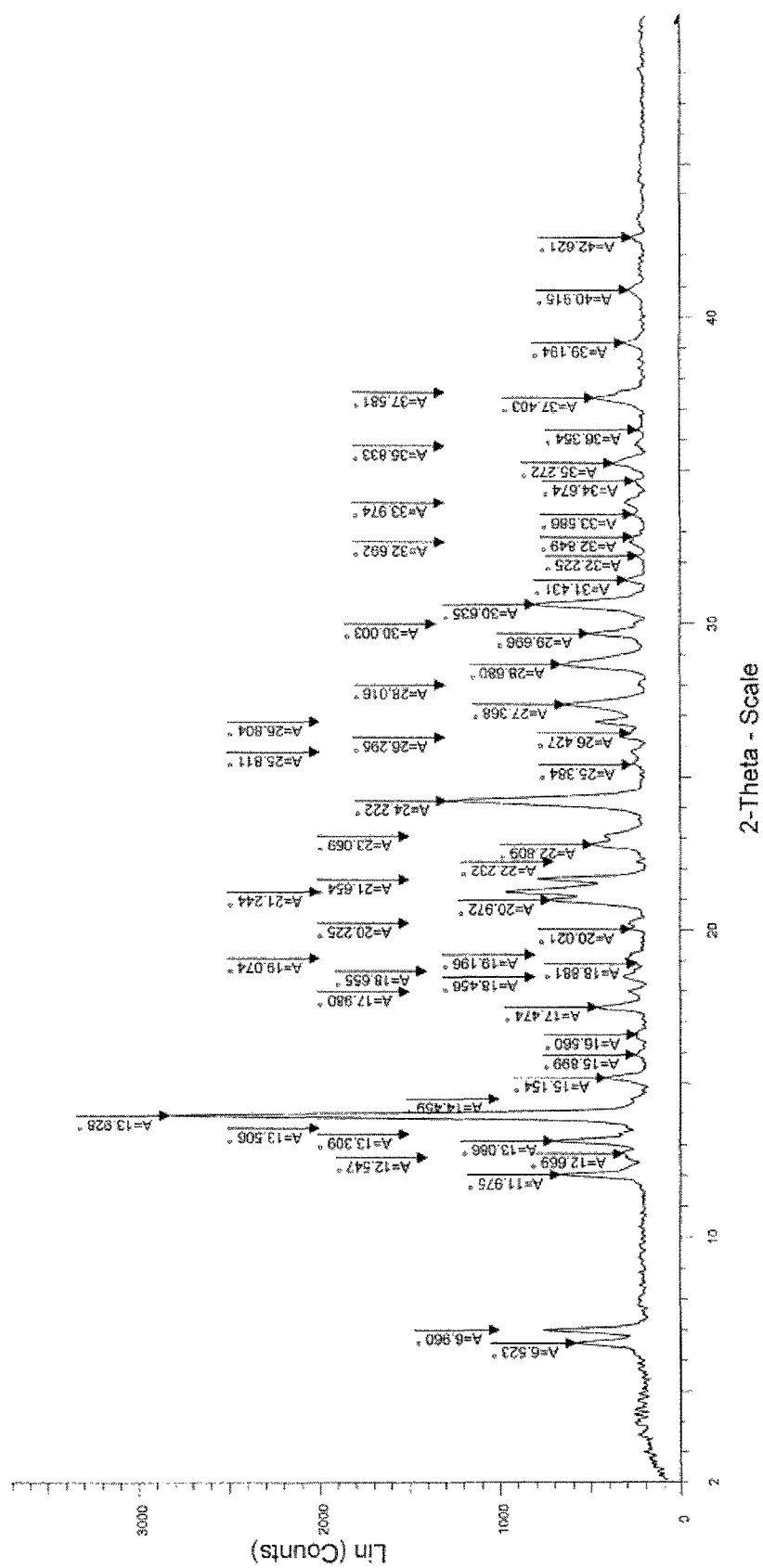

FIG. 7 is Illustration of X-ray powder diffraction (XRPD) pattern of formulation containing Neat Crystalline 5-Azacytidine Form SA-2 prepared in example 4.

X-Ray powder diffraction pattern of Neat Crystalline 5-Azacytidine Form SA-2 provided under the table below:

| Angle 2-Θ° |
|---|
| 6.523 |
| 6.96 |
| 11.975 |
| 12.547 |
| 12.669 |
| 13.086 |
| 13.309 |
| 13.506 |
| 13.928 |
| 13.928 |
| 14.459 |
| 15.154 |
| 15.899 |
| 16.56 |
| 17.474 |
| 17.98 |
| 18.456 |
| 18.655 |
| 18.881 |
| 19.074 |
| 19.196 |
| 20.021 |
| 20.225 |
| 20.972 |
| 21.244 |
| 21.654 |
| 22.232 |
| 22.809 |
| 23.069 |
| 24.222 |
| 25.384 |
| 25.811 |
| 26.295 |
| 26.427 |
| 26.804 |
| 27.368 |
| 28.016 |
| 28.68 |
| 29.696 |
| 30.003 |
| 30.635 |
| 31.431 |
| 32.225 |
| 32.692 |
| 32.849 |
| 33.586 |
| 33.974 |
| 34.674 |
| 35.272 |
| 35.833 |
| 36.354 |
| 37.403 |
| 37.581 |
| 39.194 |
| 40.915 |
| 42.621 |

DETAILED DESCRIPTION OF THE INVENTION

In an embodiment of the present invention, provides a pre-lyophilized pharmaceutical compositions comprising 5-azacytidine, in a stabilizing amount of solvent vehicle comprising at least one organic solvent selected from acetonitrile, tertiary-butyl alcohol, ethanol and acetone; and refrigerated water.

In an embodiment of the present invention, provides a crystalline 5-Azacytidine designated as Form-SA-1 characterized by an X-Ray powder diffraction pattern having at least four characteristic diffraction angle peaks at about 12.00, 12.60, 13.90, 15.15 and 31.40±0.20 2Θ°.

In an embodiment of the present invention, provides a crystalline 5-Azacytidine Form-SA-1 having water content less than 1%.

In an embodiment of the present invention, provides a process for preparing crystalline 5-Azacytidine Form SA-1, comprising the steps of—

(i) Dissolving 5-azacytidine in a solvent vehicle comprising acetonitrile and refrigerated water in the ratio of 20:80 to 60:40, to get clear solution.

(ii) Freeze-drying the solution, (iii) Isolating the Crystalline 5-Azacytidine Form SA-1.

In a preferred embodiment of the present invention, provides a process for preparing Crystalline 5-Azacytidine Form SA-1, comprising the steps of—

(i) Dissolving 5-azacytidine Form I, in a solvent vehicle comprising acetonitrile and refrigerated water in the ratio of 20:80 to 60:40, to get clear solution, at a temperature of less than 5° C., and under nitrogen purging.

(ii) Freeze-drying the solution, (iv) Isolating the Crystalline 5-Azacytidine Form SA-1.

In an embodiment of the present invention, provides a lyophilized formulation comprising crystalline 5-Azacytidine Form-SA-1, characterized by an X-Ray powder diffraction pattern having at least four characteristic diffraction angle peaks at about 12.00, 12.60, 13.90, 15.15 and 31.40±0.20 2Θ°, optionally a bulking agent; and having water content less than 2%.

In a preferred embodiment of the present invention, provides a lyophilized formulation comprising crystalline 5-Azacytidine Form-SA-1, characterized by an X-Ray powder diffraction pattern having at least four characteristic diffraction angle peaks at about 12.00, 12.60, 13.90, 15.15 and 31.40±0.20 2Θ°, optionally a bulking agent; and having water content less than 1%.

In an embodiment of the present invention, provides a process for preparing lyophilized formulation comprising Crystalline 5-Azacytidine Form SA-1, characterized by the steps:

(i) Dissolving optional bulking agent selected from mannitol, sorbitol, lactose, sucrose, or any mixtures of two or more thereof, and 5-azacytidine Form I, in a stabilizing amount of solvent vehicle comprising acetonitrile and refrigerated water; in the ratio of 20:80 to 60:40.

(ii) Lyophilizing the solution obtained from step (i);

wherein the said lyophilized formulation having 1-β-D-ribofuranosyl-3-guanylurea (RGU) impurity not more than 0.2% and total impurities not more than 2%.

In an embodiment of the present invention, provides a crystalline 5-Azacytidine designated as Form-SA-2, characterized by an X-Ray powder diffraction angle peaks at about 6.9, 14.0, 17.9 and 24.2°+0.20 2Θ°, and having water content less than 1%.

In an embodiment of the present invention, provides a process for preparing lyophilized formulation comprising Crystalline 5-Azacytidine Form SA-2, characterized by the steps:

(i) Dissolving optional bulking agent and 5-azacytidine in a solvent vehicle comprising tertiary butanol and refrigerated water in the ratio of 30:70.

(ii) Freeze-drying the solution, (iii) Isolating the Crystalline 5-Azacytidine Form SA-2.

In an embodiment of the present invention, provides a lyophilized formulation comprising crystalline 5-Azacytidine Form-SA-2, characterized by an X-Ray powder diffraction pattern having at least four characteristic diffraction angle peaks at about 6.9, 14.0, 17.9 and 24.2°±0.20 2θ°, optionally a bulking agent; and having water content less than 1%.

In an embodiment of the present invention, relates to a lyophilized formulation comprising 5-Azacytidine Form SA-1 or 5-Azacytidine Form SA-2 for parenteral administration, in a sterile vessel is provided, comprising 5-azacytidine for administration to a subject in need thereof. The sterile vessel comprising a pharmaceutical formulation according to the present invention; for example, may be a vial, syringe, or ampoule.

In an embodiment of the present invention, relates to methods of using the lyophilized formulation comprising 5-Azacytidine Form SA-1 or 5-Azacytidine Form SA-2 for parenteral administration, provided herein to treat diseases activity in the dosage form. Hence, the water content of a formulation may impact the stability of the product.

The terms "Neat Crystalline 5-Azacytidine Form SA-1" or "Neat Crystalline 5-Azacytidine Form SA-2", indicate the crystalline forms of 5-Azacytidine prepared by lyophilization without any bulking agents.

Two major degradants have been observed due to hydrolysis. The hydrolytic pathway leads to the formation of an initial N-formyl compound hydrolysis product "RGU-CHO," which is a reversible reaction and the compounds are in equilibrium with each other. This is followed by ring opening and loss of formic acid which results in formation of an amine compound "RGU," which is an irreversible reaction. RGU-CHO is N-(formylamidino) N'-β-D-ribofuranosylurea ("N-formyl compound" below) and RGU is 1-β-D-ribofuranosyl-3-guanylurea ("amine compound" below).

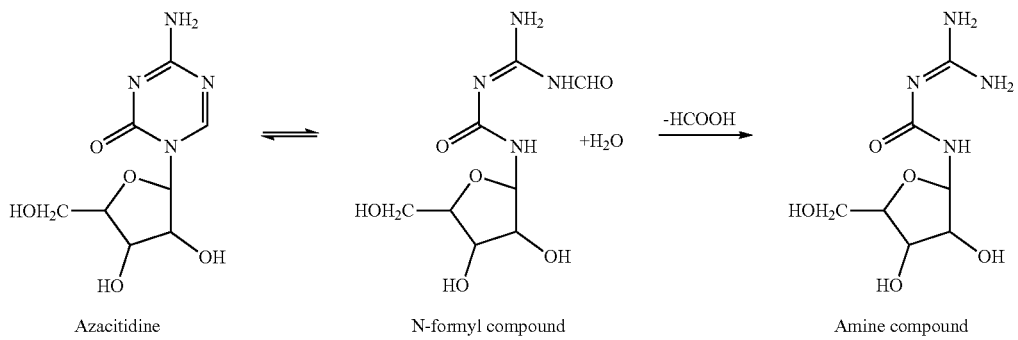

Azacitidine        N-formyl compound        Amine compound or disorders including, e.g., cancer, disorders related to abnormal cell proliferation, hematologic disorders, or immune disorders, among others. In certain embodiments, the pharmaceutical compositions of 5-azacytidine which are parenterally administered to subjects in need thereof to treat a cancer or a hematological disorder, such as, for example, Myelodysplastic syndromes (MDS), acute myelogenous leukemia (AML).

The term "formulation" as used in the context of the present invention refers to any of various dosage forms suitable for administration of a drug, such as parenterally, intraperitoneally, intravenously, intraarterially, intramuscularly, subcutaneously, etc.

The term "pharmaceutically acceptable" refers to an ingredient that is useful in preparing a pharmaceutical composition that is generally safe, non-toxic, and neither biologically nor otherwise undesirable, and includes those acceptable for veterinary use as well as human pharmaceutical use.

The term "organic solvent" means an organic material, usually a liquid, capable of dissolving other substances. In different aspects of this embodiment, the organic solvent selected from acetonitrile, tertiary-butyl alcohol, Ethanol, Acetone, Dimethylsulfoxide (DMSO) and Dimethylformamide (DMF).

5-azacytidine hydrolyzes quickly in water, and this is dependent on pH and temperature. It has been observed that, due to hydrolysis, around nine solid state forms have been identified: five polymorphic forms, three psueodpolymorphic forms and an amorphous form. Polymorphism could be of importance since speed of dissolution of azacitidine could affect its degradation. Azacitidine rapidly degrades in aqueous solutions via hydrolysis, and due to this instability a lyophilized dosage form was developed to minimize water The term "Impurity-1" as referred in the specification relates to 4-amino-1,3,5-triazine-2-(1H)-one or also known as 5-Azacytosine.

The term "Impurity-2" as referred in the specification relates to 1-O-Acetyl-2,3,5-Tri-O-benzoyl-β-D-ribofuranose.

The term "Impurity-3" as referred in the specification relates to 1-(2,3,5-Tri-O-benzoyl-β-D-ribifuranosyl)-4-amino-1,2-dihydro-1,3,5-triazin-2-one.

The term "Total impurity" as referred in the specification relates to sum of all known impurities like "Impurity-1", "Impurity-2", "Impurity-3" and RGU; but excluding RGU-CHO.

As used herein "stabilizing amount of solvent vehicle" means the ratio of organic solvent and water which would reduce the level of degradation products of 5-azacytidine in the invention compositions. For example, a concentration of 30:70 of stabilizing amount of solvent vehicle would limit the levels of 1-β-D-ribofuranosyl-3-guanylurea (RGU) is NMT 0.2% w/w of 5-AZT.

The term "water for injections or WFI" as referred in the specification relates to distilled or sterile water for injection or saline or physiological saline or 0.9% Sodium Chloride Injection or Lactated Ringer's Injection.

The term "refrigerated water or refrigerated water for injection" referred in the specification relates to having a temperature of less than about 8° C., or a temperature of between about 2° C. to 8° C. or a temperature of about 5° C.

Injectable formulations can be prepared in conventional forms, either as liquid solutions or suspensions, solid forms suitable for solubilization or suspending in liquid prior to injection, or as emulsions. Sterile injectable formulations can be prepared according to techniques known in the art using suitable carriers, dispersing or wetting agents, and/or suspending agents. The injectable formulations may be sterile injectable solutions or suspensions in a nontoxic, parenterally acceptable diluent or solvent. Among the acceptable vehicles and solvents that may be employed are water, Ringer's solution and isotonic sodium chloride solution. In addition, fixed oils, fatty esters or polyols are conventionally employed as solvents or suspending media.

The technique known as lyophilization is sometimes employed to process injectable pharmaceuticals that exhibit poor active ingredient stability in aqueous solutions.

Lyophilization processing is suitable for injectables because it can be conducted under sterile conditions, which is a primary requirement for parenteral dosage forms. Cryoprotectants are excipients whose primary function is to protect the active constituent during a freezing process. Cryoprotectants in the present invention include bulking agents that may be used in the invention.

Lyophilization or freeze-drying is a process in which water is removed from a product after it is frozen and placed under a vacuum, allowing the ice to change directly from a solid to a vapor, without passing through a liquid phase. The process consists of three separate, unique, and interdependent processes; a freezing phase, a primary drying phase (sublimation), and a secondary drying phase (desorption). These processes may be optimized to enhance the product stability as well as decrease the manufacturing costs.

Freezing Phase:

A primary function of the freezing phase is to ensure that the entire container having the complex solution is completely frozen, prior to proceeding to a subsequent phase. Additionally, it is usually desired that these containers freeze in a uniform manner. While there are different ways that this can be accomplished, one option is to chill the containers after they are loaded onto the lyophilizer shelves and holding for 30-60 minutes prior to initiation of the freezing cycle. It is generally not practical to equilibrate the shelves to a freezing temperature, because of frost accumulation during the filling and loading of the containers.

Primary Drying Phase:

Once the formulation is brought to the desired frozen state, primary drying via sublimation can proceed. The primary drying phase involves the removal of bulk water at a product temperature below the ice transition temperature under a vacuum (pressures typically between 50-300 mTorr). This phase can be a critical one for stabilizing an active. The goal is to identify the glass transition temperature (Tg') for the formulation. The Tg' is the temperature at which there is a reversible change of state between a viscous liquid and a rigid, amorphous glassy state. One can measure the Tg' of candidate formulations using a differential scanning calorimeter (DSC), in particular with modulated DSC. Generally, the collapse temperature is observed to be about 2-5° C. greater than the Tg'. Hence, the shelf temperature is set such that the target product temperature is maintained near or below the Tg' of the formulation throughout the removal of solvent during the primary dry phase.

As the solvent is progressively removed from the formulation containers, the product temperature will approach and reach the shelf temperature since it is no longer cooled by water sublimation. To optimize the duration of the primary dry phase, the removal of solvent vapor can be tracked using a moisture detector, or by monitoring the decrease in pressure difference between a capacitance manometer and a thermocouple pressure gauge or by a pressure drop measurement. The optimization of the primary dry cycle involves a removal of solvent as quickly as possible without causing cake collapse and subsequent product instability.

Secondary Drying Phase:

The secondary drying phase is the final segment of the lyophilization cycle, where residual moisture is removed from a formulation's interstitial matrix by desorption with elevated temperatures and/or reduced pressures. The final moisture content of a lyophilized formulation, which can be measured by Karl Fischer or other methods, is important because if the solid cake contains too much residual moisture, the stability of the active can be compromised. Hence, it is imperative that one achieves a moisture level as low as possible.

To accomplish a low residual moisture, the shelf temperature is typically elevated to accelerate desorption of water molecules. The duration of the secondary drying phase is usually short. When microstructure collapse occurs, the residual moisture is generally significantly greater than desired. One alternative is to purge the sample chamber of the lyophilizer with alternating cycles of an inert gas such as nitrogen, to facilitate displacement of bound water. However, another solution is to properly formulate the drug product and run an optimal lyophilization cycle.

The advantages of lyophilization include: ease of processing a liquid, which simplifies aseptic handling; enhanced stability of a dry powder; removal of water without excessive heating of the product; enhanced product stability in a dry state; and rapid and easy dissolution of reconstituted product. The product is dried without elevated temperatures, thereby eliminating adverse thermal effects, and then stored in the dry state in which there are relatively few stability problems.

Additionally, freeze dried products are often more soluble, dispersions are stabilized, and products subject to degradation by oxidation or hydrolysis are protected.

Pharmaceuticals to be freeze dried are frequently in aqueous solutions, ranging from about 0.01 to 40% by weight concentrations of total solids. Usually, an improvement in stability of the lyophilizate, compared to a solution, is due to the absence of water in the lyophilizate.

A pharmacologically active constituent of many pharmaceutical products is present in such small quantities that, if freeze dried alone, it may not give a composition of suitable mass, and in some cases its presence would be hard to detect visually. Therefore, excipients are often added to increase the amount of solids present. In most applications it is desirable for a dried product cake to occupy essentially the same volume as that of the original solution. To achieve this, the total solids content of the original solution is frequently about 10 to 25% by weight. Bulking substances that are useful for this purpose, often in combination, include, but are not limited to, sodium or potassium phosphates (monobasic potassium phosphate, potassium dihydrogen phosphate, etc.), citric acid, tartaric acid, gelatin, lactose and other carbohydrates such as dextrose, mannitol and dextran, and occasionally preservatives. Various excipients contribute appearance characteristics to the cake, such as dull and spongy, sparkling and crystalline, firm or friable, expanded or shrunken, and uniform or striated. Therefore formulations of a composition to be freeze dried should be a result of consideration not only of the nature and stability characteristics required during the liquid state, both freshly prepared and when reconstituted before use, but also the characteristics desired in the final lyophilized cake.

The injectable pharmaceutical formulations may optionally include one or more other pharmaceutically acceptable excipients. The pharmaceutically acceptable excipients may include any one or more of: antibacterial preservatives, such as one or more of phenylmercuric nitrate, thiomersal, benzalkonium chloride, benzethonium chloride, phenol, cresol, and chlorobutanol; antioxidants including one or more of ascorbic acid, sodium sulfite, sodium bisulfite and sodium metabisulfite; chelating agents such as ethylenediamine tetraacetic acid (EDTA); buffers including one or more of acetate, citrate, tartarate, phosphate, benzoate and bicarbonate buffers; tonicity contributors including one or more of sodium chloride, potassium chloride, dextrose, mannitol, sorbitol and lactose; and alkaline substances including one or more of sodium hydroxide, potassium hydroxide, sodium carbonate and meglumine.

In aspects the invention includes kits provided for delivery of the azacitidine or its salts. A kit according to the present invention comprises a container holding the drug composition, a sterile reconstitution vehicle, and a sterile syringe.

Certain specific aspects and embodiments of the invention will be further described in the following examples, which are provided only for purposes of illustration and are not intended to limit the scope of the invention in any manner.

Example 1: Azacitidine for Injection 100 mg/Vial

| S. No. | Ingredients | Qty./mL |
|---|---|---|
| 1 | 5-Azacytidine Form I | 5.0 mg |
| 2 | Mannitol [Pyrogen free] | 5.0 mg |
| 3 | Acetonitrile | 0.5 mL |
| 4 | Milli Q water | Q.s to 1.0 mL |

Batch Size: 200 vials

Brief Method of Preparation:
1. 30% of precooled Milli-Q water (5° C.) of required batch Size was collected in cleaned Duran bottle and the temperature was maintained at 5° C. throughout the manufacturing process.
2. Dispensed quantity of acetonitrile was added to the above step and stirred for 5 minutes and the solution was cooled to 5° C.
3. Weighed quantity of Mannitol was added to the above step and stirred to get a clear solution.
4. Weighed quantity of 5-azacytidine was added to the above step and stirred to get the clear solution.
5. Volume was made up to 100% with cool Milli-Q water and stirred for 5 minutes.
6. The solution of step 5 was filtered through 0.2μ PES Filter and filtrate was filled into 30 ml/20 mm flint moulded Vial with a fill volume of 20.0 mL, half stoppered with dark grey Bromobutyl rubber stopper and loaded into precooled Lyophilizer.
7. The Lyophilization was carried out as per below recipe.

| Step | Temperature ° C. | Ramp duration (min) | Soak duration (min) | Pressure (mTorr) | Pressure (mbar) |
|---|---|---|---|---|---|
| Freezing | | Precooling at −5° C. | | | |
| 1 | −15 | 60 | 60 | — | — |
| 2 | −40 | 60 | 240 | — | — |
| Primary Drying | | | | | |
| 3 | −15 | 150 | 800 | 200 | 0.2666 |
| 4 | −5 | 90 | 800 | 200 | 0.2666 |
| 5 | 5 | 60 | 360 | 100 | 0.1333 |
| 6 | 25 | 60 | 500 | 100 | 0.1333 |
| Secondary Drying | | | | | |
| 8 | 45 | 60 | 900 | 50 | 0.0667 |
| | | 540 | 3660 | | |
| | | 4200 | | | |
| Total cycle duration | | 70 Hours | | | |

8. After completion of the cycle, vacuum was breakdown through Nitrogen then the vials were fully stoppered and unloaded from Lyophilizer. The unloaded vials were sealed using aluminum seals.

A placebo formulation of example 1 is prepared with the same formula and manufacturing process by excluding 5-azacytidine.

Chemical stability is tested for both example 1 & it's corresponding placebo formulation by storing the lyophilized vials under various conditions: 25° C. and 60% relative humidity ("A"); 40° C. and 75% relative humidity ("B"); and 60° ("C"); for one month. Impurity analyses are done before storage ("Initial") and after storage, and are expressed as percentages of the label 5-azacytidine content.

Further, example 1 & its corresponding placebo formulations were subjected to X-ray powder diffraction (XRPD) and as illustrated in FIGS. 2&3; it was observed that 5-azacytidine SA-1 found in the example 1 formulation.

The chemical stability and water content results are given below:

| | | | Related Substances | | | | | |
|---|---|---|---|---|---|---|---|---|
| Tests | Assay | Impurity-1 | Impurity-2 | Impurity-3 | RGU-CHO | RGU | Max individual unknown impurity | Total Impurities |
| Specification | 90.0%-110.0% | NMT 0.2% | NMT 0.2% | NMT 0.2% | NMT 1.0% | NMT 1.0% | NMT 0.2% | NMT 2.0% |
| Initial | 96.8% | ND | ND | ND | 0.12 | ND | 0.04 | 0.09 |
| 1 Month 40° C./75% RH | 97.0% | ND | ND | ND | 0.03 | ND | 0.03 | 0.05 |
| 2 Month 40° C./75% RH | 97.8% | ND | ND | ND | 0.05 | ND | 0.04 | 0.14 |
| 3 Month 40° C./75% RH | 97.4% | ND | ND | ND | 0.10 | ND | 0.12 | 0.18 |
| 1 week 60° C. | 98.0% | ND | ND | ND | 0.05 | ND | 0.03 | 0.08 |
| 6 Month 25° C./60% RH | 99.0% | ND | ND | ND | 0.07 | 0.09 | 0.03 | 0.14 |

ND—Not Detected.

| Tests | Water content |
|---|---|
| Initial | 0.62% |
| 1 Month 40° C./75% RH | 0.75% |
| 2 Month 40° C./75% RH | 0.73% |
| 3 Month 40° C./75% RH | 0.56% |
| 1 week 60° C. | 0.76% |

Example 2: Azacitidine for Injection 100 mg/Vial

| S. No. | Ingredients | Qty./mL |
|---|---|---|
| 1 | Azacytidine | 5.0 mg |
| 2 | Mannitol [Pyrogen free] | 5.0 mg |
| 3 | T-Butanol | 0.3 mL |
| 4 | Milli Q water | Q.s to 1.0 mL |

Batch Size: 200 vials

Brief Method of Preparation:
1. 30% of precooled Milli-Q water (5° C.) of required batch Size was collected in cleaned Duran bottle and the temperature was maintained at 5° C. throughout the manufacturing process.
2. Dispensed quantity of tertiary-butyl alcohol was added to the above step and stirred for 5 minutes and the solution was cooled to 5° C.
3. Weighed quantity of Mannitol was added to the above step and stirred to get a clear solution.
4. Weighed quantity of 5-azacytidine was added to the above step and stirred to get the dispersion, and stirred till clear solution is formed.
5. Volume was made up to 100% with cool Milli-Q water and stirred for 5 minutes.
6. The solution of step 5 was filtered through 0.2μ PES Filter and filtrate was filled into 30 ml/20 mm flint moulded Vial with a fill volume of 20.0 mL, half stoppered with dark grey Bromobutyl rubber stopper and loaded into precooled Lyophilizer.
7. The Lyophilization was carried out according to the lyophilization recipe of example-1
8. After completion of the cycle, vacuum was breakdown through Nitrogen then the vials were fully stoppered and unloaded from Lyophilizer. The unloaded vials were sealed using aluminum seals.

A placebo formulation of example 2 is prepared with the same formula and manufacturing process by excluding 5-azacytidine.

Further, example 2 & its corresponding placebo formulations were subjected to X-ray powder diffraction (XRPD) and as illustrated in FIGS. 4&5; it was observed that 5-azacytidine SA-2 found in the example 2 formulation.

Example 3: Preparation of Lyophilized Formulation Containing Neat 5-Azacytidine Form-SA-1

| S. no. | Ingredients | Qty./mL |
|---|---|---|
| 1 | 5-Azacytidine Form I | 5.0 mg |
| 2 | Acetonitrile | 0.5 mL |
| 3 | Milli Q water | Q.s to 1.0 mL |

Batch Size: 200 vials

Brief Method of Preparation:
1. 30% of precooled Milli-Q water (5° C.) of required batch Size was collected in cleaned Duran bottle and the temperature was maintained at 5° C. throughout the manufacturing process.
2. Dispensed quantity of acetonitrile was added to the above step and stirred for 5 minutes and the solution was cooled to 5° C.
3. Weighed quantity of 5-azacytidine Form I was added to the above step and stirred to get the clear solution.
4. Volume was made up to 100% with cool Milli-Q water and stirred for 5 minutes.
5. The solution of step 4 was filtered through 0.2μ PES Filter and filtrate was filled into 30 ml/20 mm flint moulded Vial with a fill volume of 20.0 mL, half stoppered with dark grey Bromobutyl rubber stopper and loaded into precooled Lyophilizer.

The Lyophilization cycle was carried out as per recipe defined under Example 1.

After completion of the lyophilization cycle, vacuum was breakdown through Nitrogen then the vials were fully stoppered and unloaded from Lyophilizer. The unloaded vials were sealed using aluminum seals.

Water content of Crystalline 5-Azacytidine Form-SA-1 obtained is 0.6% w/w.

Further, example 3 formulation was subjected to X-ray powder diffraction (XRPD) and as illustrated in FIG. 6; 5-azacytidine SA-1 was found in the example 3 formulation.

Example 4: Preparation of Lyophilized Formulation Containing Neat 5-Azacytidine Form-SA-2

| S. No. | Ingredients | Qty./mL |
|---|---|---|
| 1 | Azacytidine | 5.0 mg |
| 2 | T-Butanol | 0.3 mL |
| 3 | Milli Q water | Q.s to 1.0 mL |

Batch Size: 200 vials

Brief Method of Preparation:
1. 30% of precooled Milli-Q water (5° C.) of required batch Size was collected in cleaned Duran bottle and the temperature was maintained at 5° C. throughout the manufacturing process.
2. Dispensed quantity of tertiary butanol was added to the above step and stirred for 5 minutes and the solution was cooled to 5° C.
3. Weighed quantity of 5-azacytidine Form I was added to the above step and stirred till clear solution obtained.
4. Volume was made up to 100% with cool Milli-Q water and stirred for 5 minutes.
5. The solution of step 4 was filtered through 0.2μ PES Filter and filtrate was filled into 30 ml/20 mm flint moulded Vial with a fill volume of 20.0 mL, half stoppered with dark grey Bromobutyl rubber stopper and loaded into precooled Lyophilizer.

The Lyophilization cycle was carried out as per recipe defined under Example 2.

After completion of the lyophilization cycle, vacuum was breakdown through Nitrogen then the vials were fully stoppered and unloaded from Lyophilizer. The unloaded vials were sealed using aluminum seals.

Water content of Crystalline 5-Azacytidine Form-SA-2 obtained is 0.7% w/w.

Further, example 4 formulation was subjected to X-ray powder diffraction (XRPD) and as illustrated in FIG. 7; 5-azacytidine SA-2 was observed in the example 4 formulation.

The invention claimed is:

1. Crystalline 5-azacytidine designated as Form-SA-1 characterized by an X-ray powder diffraction pattern having at least four characteristic diffraction angle peaks at about 12.00, 12.60, 13.90, 15.15 and 31.40±0.20 2θ°.

2. Crystalline 5-azacytidine Form-SA-1 according to claim 1; wherein the water content is less than 1%.

3. A process for preparing Crystalline 5-azacytidine Form SA-1, characterized by an X-ray powder diffraction pattern having at least four characteristic diffraction angle peaks at about 12.00, 12.60, 13.90, 15.15 and 31.40±0.20 2θ°; comprising the steps of—
    (i) Dissolving 5-azacytidine in a solvent vehicle consisting of acetonitrile and refrigerated water in the ratio of 20:80 to 60:40;
    (ii) Freeze-drying the solution,
    (iii) Isolating the Crystalline 5-Azacytidine Form SA-1.

4. A process for preparing Crystalline 5-azacytidine Form SA-1 according to claim 3, wherein refrigerated water is a precooled water having temperature of less than 5° C. and dissolving of 5-azacytidine is carried out under nitrogen purging.

5. A process for preparing Crystalline 5-azacytidine Form SA-1 according to claim 3, wherein before freeze drying step, the step i) solution is stirred to get a clear solution.

* * * * *